United States Patent [19]

Dahl et al.

[11] Patent Number: 5,063,932
[45] Date of Patent: Nov. 12, 1991

[54] CONTROLLED DISCHARGE DEFIBRILLATION ELECTRODE

[75] Inventors: Roger W. Dahl, Andover; Ronald W. Heil, Jr., Roseville, both of Minn.

[73] Assignee: Mieczyslaw Mirowski, Owings Mills, Md.

[21] Appl. No.: 416,421

[22] Filed: Oct. 3, 1989

[51] Int. Cl.$^5$ .............................................. A61N 1/05
[52] U.S. Cl. .................................... 128/639; 128/642; 128/783
[58] Field of Search .......... 128/640, 642, 639, 419 D, 128/799, 798, 783, 784, 802

[56] References Cited

U.S. PATENT DOCUMENTS

| | | | |
|---|---|---|---|
| 3,380,445 | 4/1968 | Frasier | 128/639 |
| 3,568,660 | 3/1971 | Crites et al. | 128/2 |
| 3,572,344 | 3/1971 | Bolduc | 128/418 |
| 3,662,757 | 5/1972 | Blackett | 128/798 |
| 4,281,707 | 9/1981 | Heilman et al. | 128/784 |
| 4,481,953 | 11/1984 | Gold et al. | 128/786 |
| 4,567,900 | 2/1986 | Moore | 128/784 |
| 4,736,752 | 4/1988 | Munck et al. | 128/798 |
| 4,807,621 | 2/1989 | Hagen et al. | 128/798 |
| 4,817,634 | 4/1989 | Holleman et al. | 128/784 |
| 4,827,932 | 5/1989 | Ideker et al. | 128/419 |
| 4,860,769 | 8/1989 | Fogarty et al. | 128/786 |

FOREIGN PATENT DOCUMENTS 3530269 2/1987 Fed. Rep. of Germany .
2182566 5/1987 United Kingdom .

OTHER PUBLICATIONS

Yongmin Kim et al., "Optimal Electrode Designs for Electro-Surgery, Defibrillation, and External Cardiac Pacing", Sep. 1986, pp. 845–853, vol. BME-33, IEEE Transactions on Biomedical Engineering.

Primary Examiner—William E. Kamm
Assistant Examiner—Scott M. Getzow
Attorney, Agent, or Firm—Fleit, Jacobson, Cohn, Price, Holman & Stern

[57] ABSTRACT

A defibrillation electrode for implantation on or about the heart and for connection to a defibrillation system. The electrode comprises a plurality of electrically conductive elements spaced apart and electrically connected together, thus, increasing the number of discharging edges on the electrode. In a first embodiment, the electrode comprises a plurality of concentric conductive rings electrically connected together. In a second embodiment, electrode comprises a plurality of conductive planar elements electrically connected together in a generally puzzle-like configuration. In a third embodiment, the electrode comprises electrically conductive wires wrapped around the length of a cardiac catheter. In a fourth embodiment, electrically conductive wires are concentrically spiralled into a spiral patch configuration. In a fifth specific embodiment, a plurality of electrically isolated active sites are provided on the distal portion of an endocardial catheter. In all of the above embodiments, the electrical discharge of energy from the electrode to the heart surface favors the conductive edges of the electrically conductive and connected components of the electrodes. Therefore, by increasing the number of conductive edges, a more uniform distribution of energy is delivered to the heart. Furthermore, each of the electrode configurations may be constructed without an insulative backing to further increase the efficiency of discharge.

9 Claims, 3 Drawing Sheets

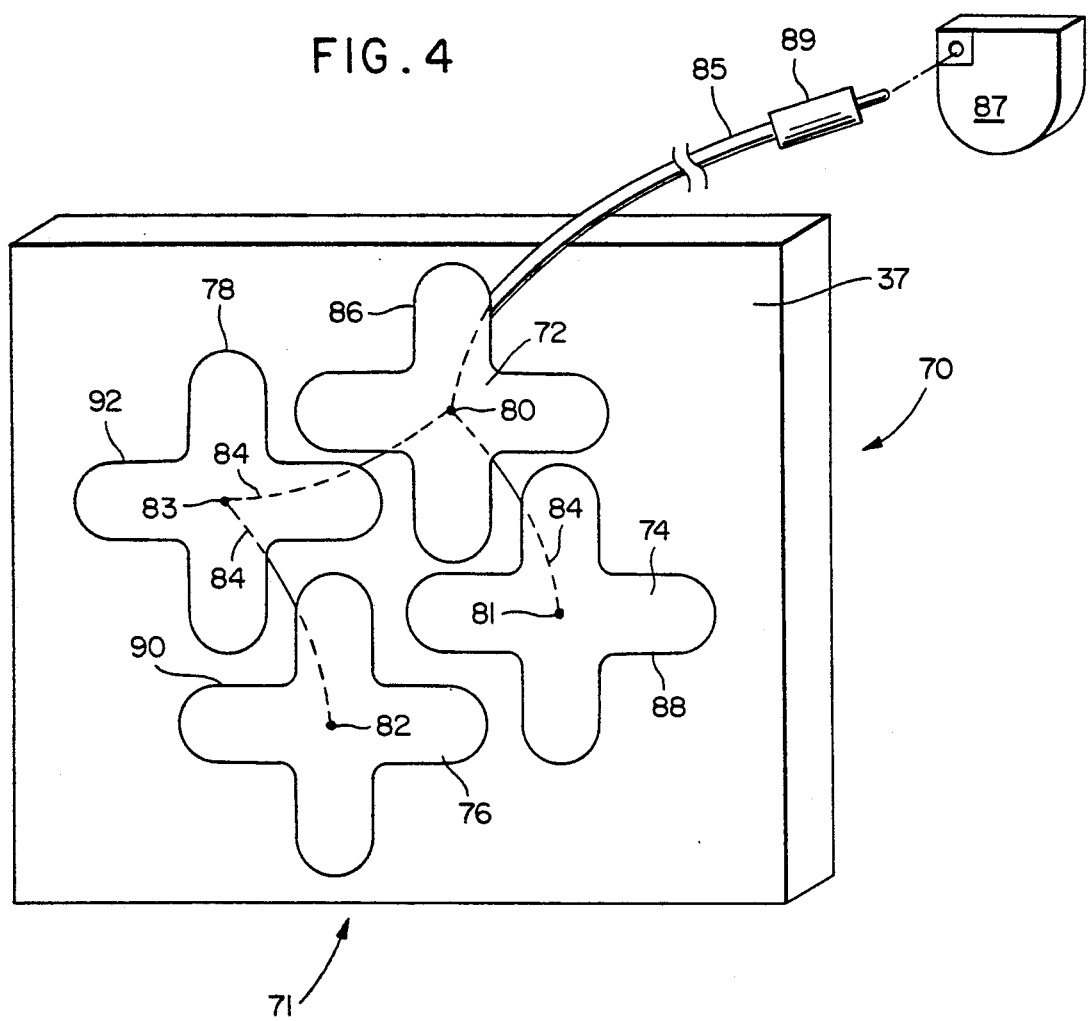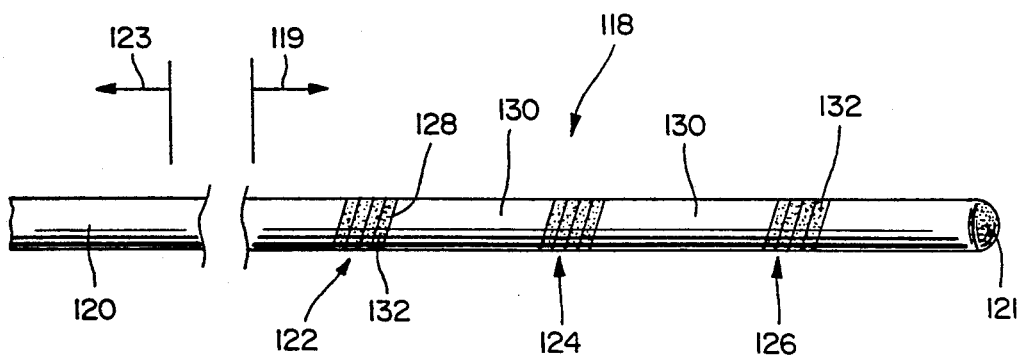

CONTROLLED DISCHARGE DEFIBRILLATION ELECTRODE

BACKGROUND OF THE INVENTION

This invention relates to an electrode for medical applications, and more particularly to an implantable cardiac cardioversion/defibrillation electrode.

Electrodes implanted in the body for electrical cardioversion or defibrillation of the heart are well known. More specifically, electrodes implanted in or about the heart have been used to reverse (i.e., defibrillate or cardiovert) certain life-threatening cardiac arrhythmias, where electrical energy is applied to the heart via the electrodes to return the heart to normal sinus rhythm. See, for example, commonly assigned U.S. Pat. No. 4,291,707 to Heilman, relating to a planar patch defibrillation electrode, and pending U.S. patent application Ser. No. 07/334,652 entitled Cardiac Defibrillation/Cardioversion Spiral Patch Electrode, filed Apr. 10, 1989.

The Heilman patent specifically discloses an implantable cardiac electrode comprised of a planar conductive material insulated completely on one side and partially on its other side. Apertures are provided around the insulated perimeter of the partially insulated side of the electrode to provide for efficient and uniform energy transfer to the heart tissue by eliminating the so called "edge-effect".

The pending application Ser. No. 07/334,652, relates to a spiral patch electrode comprised of a elongated conductor preformed to adapt a spiral planar patch configuration when deployed on or about the heart surface.

The amount of energy delivered by the electrodes to the heart during defibrillation (or cardioversion) depends on the placement of the electrodes and the ability of the electrodes to distribute the energy uniformly throughout a major portion of the heart. This energy is called the defibrillation or cardioversion energy.

For purposes of the following discussion, no distinction will be made between cardioversion and defibrillation, although the respective energy levels and timing sequences may differ. Both will be referred to as defibrillation.

SUMMARY OF THE INVENTION

The present invention relates to an electrode configuration in which the defibrillation energy is minimized by shaping the discharge electric field so that the electric energy efficiently reaches and is applied across the heart.

When electrical energy is applied between defibrillating electrodes, it has been recognized that the discharging of the energy favors electrically conductive edges on the conductive portions of the electrodes. Therefore, to increase the efficiency with which an electrode delivers energy to the heart, and to provide a uniform distribution of the energy across the heart, it has been found that such can be accomplished by way of an electrode including a plurality of conductive edges arranged in patterns to focus or control the discharge. These patterns increase the amount of edge effect in such a way as to smooth and/or direct the current distribution.

Therefore, it is a primary object of this invention to meet the above conditions by providing a defibrillation electrode having a plurality of electrically conductive edges.

It is an additional object of this invention to provide a defibrillation electrode having a discharge surface region formed into various geometrical shapes for delivering a controlled electrical discharge to the heart.

The electrode of the present invention comprises a surface of a predetermined area having a plurality of electrically conductive elements with electrically conductive edges defined by their periphery. The conductive edges are formed by either actual breaks in the conductive element or by hermetically isolating the conductive elements with an electrolysis tight barrier coating. In either case, the conductive elements are separated by some distance. The conductive elements are electrically connected together to a common lead.

In a first specific embodiment, the electrode comprises a planar surface region having a plurality of concentric conductive elements which may take the geometrical shape of a circle or a clover leaf. The concentric elements are connected together by conductive radial arms.

In a second specific embodiment, the electrically conductive elements forming the planar conductive discharge surface region of the electrode comprise a plurality of planar conductive members formed into various geometrical shapes, positioned in a manner similar to that of puzzle pieces, and electrically connected together.

The electrodes of first and second embodiments can be adapted as either epicardial patch electrodes or subcutaneous patch electrodes. As is well known in the art, epicardial electrodes are mounted on or in intimate contact with the heart while subcutaneous electrodes are mounted not in intimate contact with the heart. Further, hereinafter, the phrase "on or about the heart" is meant to include in physical contact with the heart, within the pericardial space, and subcutaneous.

In a third specific embodiment, separate electrically conductive wires are wound around a catheter and are electrically connected together to form a plurality of conductive edges. The catheter can be formed into a spiral configuration.

In a fourth specific embodiment, separate electrically conductive wires, electrically connected together, are embedded in an insulator strip which is coiled into a spiral configuration.

In a fifth specific embodiment, a plurality of electrically isolated active sites are provided on the distal portion of an endocardial catheter. Each active site comprises a plurality of turns of conductive ribbon. The catheter is designed to be inserted through one of the great veins to the inside of the heart.

The above and other objects and advantages will become more apparent when reference is made to the following description, taken in conjunction with the accompanying drawings.

BRIEF DESCRIPTION OF THE DRAWINGS

FIG. 4 is an enlarged plan view illustrating the discharge surface of the defibrillation electrode comprising the second embodiment of this invention.

FIG. 8 is a plan view illustrating the discharge surface of the defibrillation electrode of the fifth embodiment of the present invention.

DETAILED DESCRIPTION OF THE DRAWINGS

Figure 1:
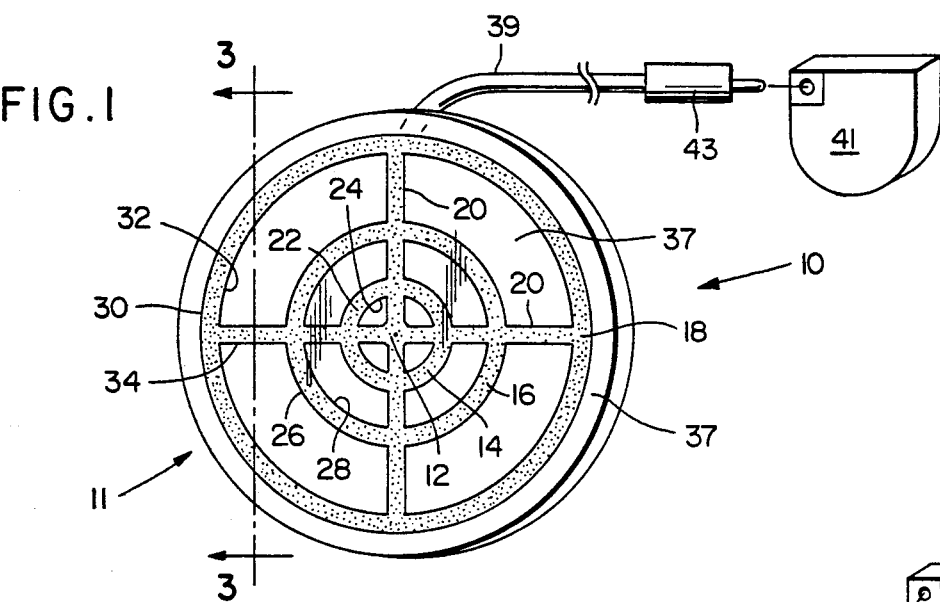
FIGS. 1 and 2 are perspective views illustrating the discharge surfaces of the defibrillation electrode comprising the first embodiment of the present invention.

Referring first to FIG. 1, a defibrillation electrode of the first embodiment of the present invention is shown at 10. Electrode 10 is shown as a circular element having a substantially planar discharge surface region 11 comprising a central conductive disk 12 encircled by spaced concentric conductive rings 14, 16, and 18. Rings 14, 16, and 18 are connected to each other and to the central conductive disk or point 12 by radial conductive arms, or spokes 20. Each conductive ring 14, 16, and 18 defines conductive edges 22 and 24, 26 and 28, and 30 and 32, respectively, on the outer and inner peripheries. In addition, conductive spokes 20 define conductive edges 34 and 36.

Figure 3:
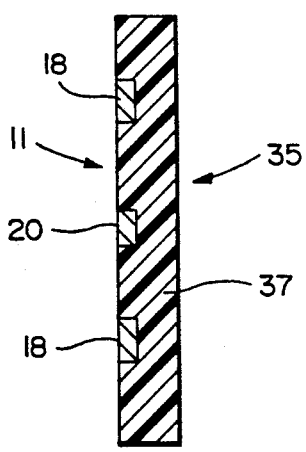
FIG. 3 is a cross-sectional view taken through line 3—3 of FIG. 1.

Referring to FIG. 3, the cross section of electrode 10 is illustrated. Insulation 37 covers the entire back surface 35 opposite the discharge surface region 11, and occupies the area defined by the concentric rings and radial spokes of the electrode. The discharge surface region 11 is a planar, or flat surface wherein the conductive rings/spokes are embedded within the insulation 37 and coplanar therewith.

Figure 2:
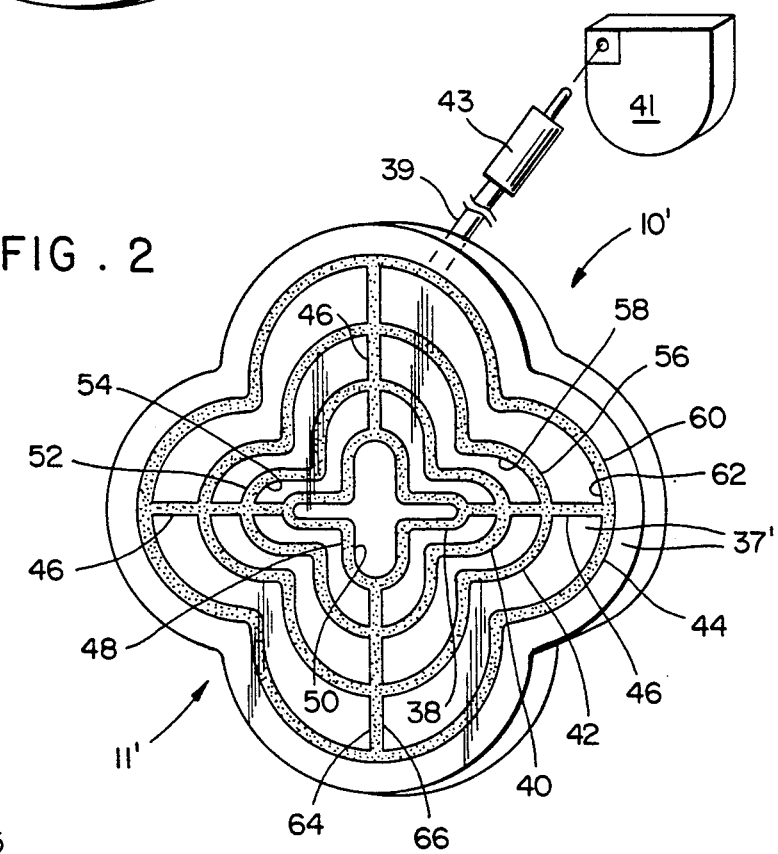

Referring now to FIG. 2, another electrode 10' of the first embodiment of the present invention is shown. Electrode 10' includes a substantially planar discharge surface region 11' comprising a central conductive ring 38 formed into the geometrical shape of a clover leaf and encircled by concentric rings 40, 42, and 44, which are also formed into the geometrical shape of a clover leaf. The rings 40, 42, and 44 are connected to each other and to the central conductive ring 38 by conductive spokes 46. Conductive rings 38, 40, 42, and 44 define outer and inner perimeter edges 48 and 50, 52 and 54, 56 and 58, and 60 and 62, respectively. In addition, conductive spokes 46 define conductive edges 64 and 66. Insulation 37' is provided around the perimeter and on the surface opposite the discharge surface region 11'; thus electrode 10' has a cross section similar to that of electrode 10 illustrated in FIG. 3.

The conductive edges on the conductive elements are formed by actual spaces or breaks in conductive material to form discrete elements or by placing a hermetically tight barrier coating over a single conductive element to create a plurality of conductive elements. The hermetic barrier coating prohibits fluid electrolytes from contacting on the conductive element, and thus establishing and maintaining the edge effect desired.

While the electrodes 10 and 10' are shown in wagon wheel and clover leaf configurations, respectively, it is considered within the scope of this invention to form a defibrillation electrode of a construction similar to that shown in FIGS. 1 and 2, but in various other geometrical shapes. Furthermore, while the type of conductive and insulative material used to form defibrillation electrodes varies, it is envisioned that electrically conductive materials such as titanium are used in constructing electrodes 10 and 10'. In addition, although the size and dimension of the electrode can be altered, the overall conductive surface area of the constructive electrode 10 or 10' is on the order of 10–100 sq. cm.

Furthermore, having found that highly efficient discharges are possible, electrodes 10 and 10', in a modified form, may be constructed and used without insulative backing 37 and 37', respectively.

In use, electrode 10 or 10' is implanted on or in the region of the heart surface, together with at least one other implanted electrode of similar or other type of construction and connected to an implanted cardioverter/defibrillator 41 by plug 43 at the end of insulated lead 39 electrically connected to the electrode as shown in FIGS. 1 and 2. The lead 39 includes an electrically conductive wire that extends through the back surface 35 of the electrode and is connected to one or more of the conductive surfaces.

When electrical energy is applied to the electrodes for generating an electric field between the implanted electrodes, the energy discharged from the electrode 10 or 10' to the heart favors the conductive edges of the electrode. Because of the number of conductive edges and the separation between edges on electrode 10 or 10', these electrodes will provide a controlled and efficient energy discharge distribution to the heart for generating the desired electric field in the heart. As such, ventricular fibrillation can be reversed with a minimum amount of energy being applied by the associated implanted cardioverter/defibrillator.

FIG. 4 shows a defibrillation electrode 70 comprising a second embodiment of the present invention. Electrode 70 includes a substantially planar surface area comprising a plurality of electrically conductive elements 72, 74, 76, and 78 formed into the geometrical shape of a clover leaf. The conductive elements 72, 74, 76, and 78 are electrically connected to each other at sites 80, 81, 82, and 83. All of these sites are connected together by conductors 84, which, in turn, are connected to lead 85 provided for connection to the implanted cardioverter/defibrillator 87 via plug 89. Each conductive element 72–78 defines outer perimeter edges 86, 88, 90, and 92, respectively. Insulation 37 occupies the periphery of the electrode and the surface opposite the discharge surface region 71, and the area surrounding the conductive elements, similar to electrodes 10 and 10' as shown in FIGS. 1 and 2. The conductive elements 72, 74, 76 and 78 are analogous to jigsaw pieces embedded in the insulation 37 and coplanar therewith.

The quantity and geometrical shape of the conductive elements which comprise electrode 70 may vary. However, it is anticipated that the overall dimensions of electrode 70 be equivalent to that of electrodes 10 and 10'.

While electrodes 10, 10' and 70 are described as mounted epicardially, the same principles can be applied to subcutaneous patch electrodes. These latter electrodes are mounted beneath the skin but not in intimate contact with the heart. As mentioned above, "on or about the heart" is meant to include the positioning of an electrode in intimate contact with the heart, within the pericardial space, and subcutaneous implantation.

When electrical energy is applied to electrode 70 against at least one other energized electrode of similar or different construction, all of the conductive elements comprising the electrode 70 discharge energy from their planar surfaces and their perimeter edges. Thus, the plurality of edges on electrode 70 combine to deliver a controlled charge distribution to the tissue near which it is implanted, for generating a desired electric field across the heart in conjunction with the other implanted electrodes.

Figure 5:
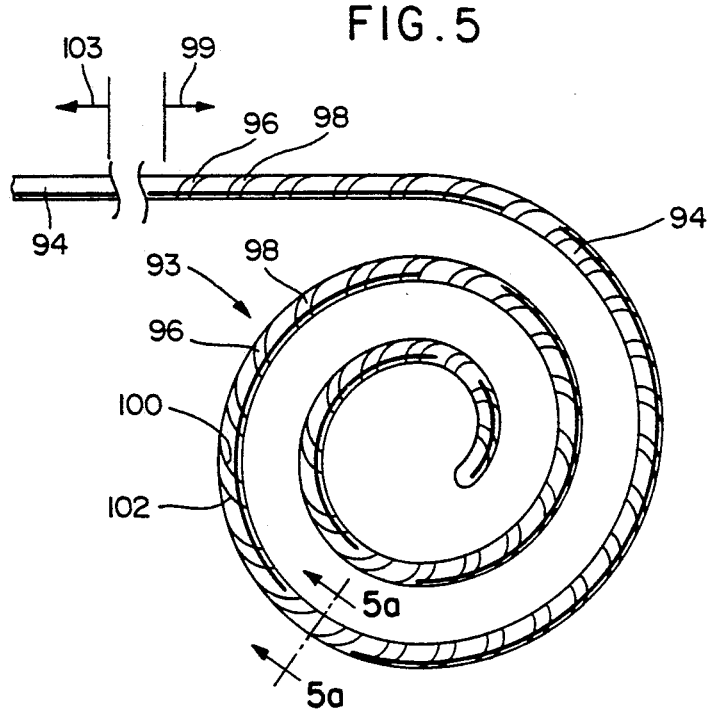
FIG. 5 is a plan view of a defibrillation electrode of the third embodiment of the present invention.
Figure 5A:
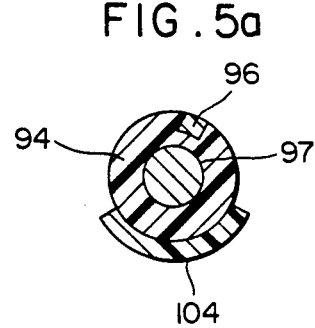
FIG. 5a is a cross-sectional view taken through line 5a—5a of FIG. 5.

Referring to FIGS. 5 and 5a, defibrillation electrode 93 of a third embodiment of the present invention is shown. Electrode 93 comprises a conventional cardiac catheter 94 having a distal active portion 99 and a proximal lead portion 103. Electrode 93 has conductive wires 96 and 98 spaced apart and alternatingly embedded around a distal active portion 99 of catheter 94. A guide or through wire 97 is provided to guide the catheter 94 to a desired location. Electrode 93 is designed to be implanted on or about the heart surface by being coiled in the configuration shown in FIG. 5 and discharged against another implanted electrode of similar or other type of construction. That is, the catheter 94 is coiled in a generally planar configuration at its distal portion. Each conductive wire 96 and 98 has conductive edges 100 and 102. The conductive wires 96 and 98 are electrically connected together at some site along the catheter 94, or at the cardioverter/defibrillator, although not specifically illustrated.

As shown in FIG. 5a, insulation 104 is provided along the length of catheter 94 on the surface portion facing away from the heart when implanted about the heart. However, the insulation 104 may be excluded from electrode 93 similar to the modified structures of electrodes 10 and 10'.

In operation, electrical energy is delivered to electrode 93 against an opposing energized electrode of similar or other construction; the electrical energy is discharged along the surfaces of conductive wires 96 and 98 and through conductive edges 100 and 02 along the length of the catheter 94. As such, the increased amount of conductive edges created by the spiral catheter 94 provides for a controlled energy discharge to the heart. To increase the number of conductive edges along the length of the catheter 94, it is possible to wind additional conductive wires around the catheter 94, although only two are illustrated.

Figure 6:
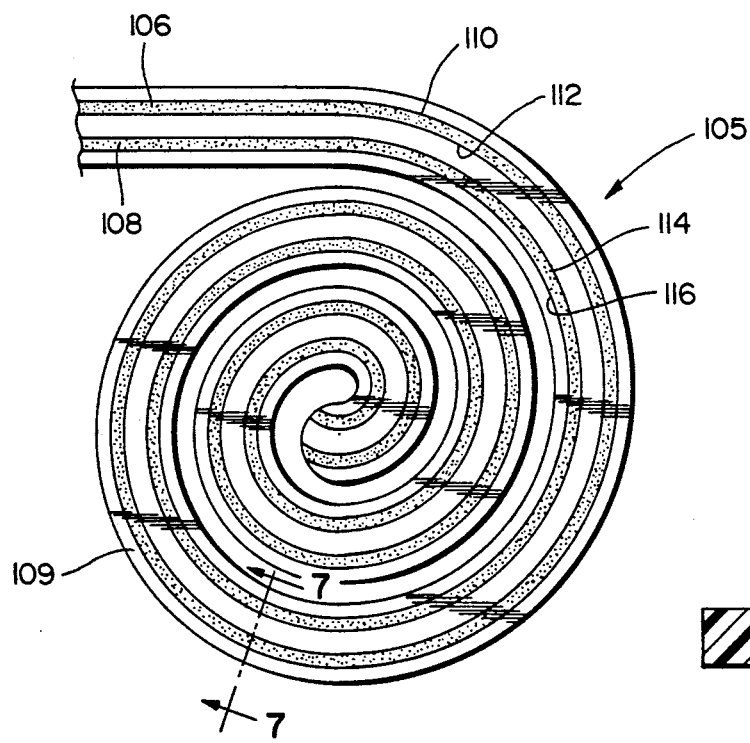
FIG. 6 is a plan view illustrating the discharge surface of the defibrillation electrode of the fourth embodiment of the present invention.
Figure 7:
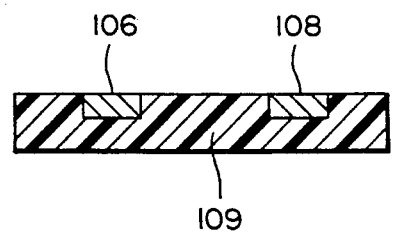
FIG. 7 is a cross-sectional view taken through lines 7—7 of FIG. 6.

FIGS. 6 and 7 show another embodiment of the defibrillation electrode of this invention. Electrode 104 comprises concentric spirals 106 and 108 of electrically conductive wire embedded in insulation 109. The wires 106 and 108 are electrically connected at some site along their length or at the cardioverter/defibrillator, although not specifically illustrated. Similar to electrode 93, the insulation 109 may be excluded from the back of electrode 105. Wires 106 and 108 include outer and inner perimeter conductive edges 110 and 112, and 114 and 116.

When implanted on or about the heart, wires 106 and 108 are arranged to assume the concentric spiral configuration as shown in FIG. 6. Electrical energy delivered to electrode 105 is discharged through the wires 106 and 108 at their respective surfaces and at their conductive edges 110–116. As a result, a controlled energy discharge distribution is achieved in the region of the heart near electrode 105.

FIG. 8 illustrates another embodiment of the present invention applying the same principles to an endocardial catheter electrode 118. Electrode 118 comprises an elongated endocardial catheter 120 preferably formed of flexible insulative material along its outer surface. The catheter has a distal active portion 119 and a proximal lead portion 123. At the distal portion of the distal active portion 119 supports a pacing tip 121 and active sites 122, 124, and 126. Each active site comprises multiple turns of conductive ribbon 128. The ribbon 128 is preferably formed of a titanium-platinum conductive material. The active sites 122, 124, and 126 are separated by spaces 130. The spaces 130 electrically isolate adjacent sites. Further, within each active site, the space between adjacent turns of the ribbon 128 is filled with an insulative material 132 to further electrically isolate adjacent turns of the ribbon 128. The insulative material 132 does not cover the exposed faces of the turns of the ribbon 128. Each active site is connected in common by an internal conductor (not shown) to a source of electrical energy.

Electrode 118 is designed to be inserted through one of the great veins leading to the heart, such as for example, the superior vena cava. The catheter 120 is inserted so that the active portion 119 is inside the heart.

The above description is intended by way of example only, and is not intended to limit the invention in any way except as set forth in the following claims.

We claim:

1. An electrode for implantation on or about the heart for connection to a defibrillation/cardioversion system, said electrode comprising:

a discharge surface region having a predetermined surface area for delivering energy to the heart, said discharge surface region being a fixed planar surface and comprising a plurality of independent electrically conductive segments each for discharging directly to the heart, said conductive segments having a plurality of electrically conductive edges and being arranged in said discharge surface region so that conductive edges of adjacent conductive segments do not overlap for maintaining a gap between conductive edges and forcing electrical discharge at said conductive edges to control the electrical discharge across said discharge surface region, said conductive segments being electrically in common and adapted to be connected to said defibrillation cardioversion system.

2. The electrode of claim 1 and further comprising an insulation element covering the surface of said electrode opposite said discharge surface region.

3. The electrode of claim 1, wherein said electrically conductive segments comprise a central conductive disk or point encircled by spaced concentric circular conductive rings.

4. The electrode of claim 1, wherein said electrically conductive segments comprise a central conductive piece formed into the geometrical shape of a clover leaf and encircled by spaced concentric conductive rings also formed into the geometrical shape of a clover leaf.

5. The electrode of claim 1, wherein said plurality of conductive segments are formed by placing an electrolysis tight barrier on a larger single conductive segment.

6. The electrode of claim 1, wherein said plurality of electrically conductive segments are planar pieces of conductive material formed into the geometrical shape of a clover leaf.

7. The electrode of claim 1, wherein said plurality of independent electrically conductive segments are arranged in a predetermined pattern in said discharge surface region so that the conductive edges of said electrically conductive segments provide a smooth and uniform electrical discharge distribution across said discharge surface region.

8. The electrode of claim 1, wherein said plurality of independent electrically conductive segments are arranged in a predetermined pattern in said discharge surface region so that the conductive edges of said electrically conductive segments focus electrical discharge across said discharge surface region in a desired direction toward the surface of the heart.

9. The electrode of claim 1, wherein said electrically conductive segments comprise a plurality of electrically conductive wires each being spaced apart and concentrically spiralled about a common point to form a planar concentric spiral configuration.

* * * * *